United States Patent
Stockham

(10) Patent No.: US 7,135,196 B2
(45) Date of Patent: Nov. 14, 2006

(54) IRON COMPOSITIONS

(75) Inventor: Michael Arthur Stockham, Saffron Walden (GB)

(73) Assignee: Vitra Pharmaceuticals Limited, Saffron Walden Essex (GB)

( * ) Notice: Subject to any disclaimer, the term of this patent is extended or adjusted under 35 U.S.C. 154(b) by 115 days.

(21) Appl. No.: 10/380,751

(22) PCT Filed: Sep. 10, 2001

(86) PCT No.: PCT/GB01/04052

§ 371 (c)(1),
(2), (4) Date: Jul. 28, 2003

(87) PCT Pub. No.: WO02/24196

PCT Pub. Date: Mar. 28, 2002

(65) Prior Publication Data
US 2004/0029853 A1 Feb. 12, 2004

(30) Foreign Application Priority Data
Sep. 19, 2000 (GB) ................. 0022881.7
Mar. 21, 2001 (GB) ................. 0107031.7

(51) Int. Cl.
A61K 31/295 (2006.01)
A61K 31/351 (2006.01)
A61K 31/355 (2006.01)
A61K 33/26 (2006.01)
A61K 9/14 (2006.01)
A61P 7/06 (2006.01)

(52) U.S. Cl. .............. 424/648; 424/489; 424/641; 424/643; 514/184; 514/249; 514/460; 514/494; 514/502; 514/574; 514/814; 514/951

(58) Field of Classification Search ............ 514/184, 514/460, 502, 574, 814, 815; 424/648, DIG. 6
See application file for complete search history.

(56) References Cited

U.S. PATENT DOCUMENTS

| 3,130,204 | A | 4/1964 | Tate et al. ........... 260/345.9 |
| 3,365,469 | A | 1/1968 | Tate et al. ........... 260/345.9 |
| 3,592,889 | A | 7/1971 | Lindvall et al. ........ 424/147 |
| 4,018,907 | A | 4/1977 | Scarpellino .......... 426/250 |
| 4,279,936 | A | 7/1981 | Jones et al. .......... 426/265 |
| 4,550,101 | A | 10/1985 | Hider et al. .......... 514/188 |
| 4,575,502 | A | 3/1986 | Hider et al. .......... 514/184 |
| 4,585,780 | A | 4/1986 | Hider et al. .......... 514/348 |
| 4,587,240 | A | 5/1986 | Hider et al. .......... 514/188 |
| 4,650,793 | A | 3/1987 | Hider et al. .......... 514/188 |
| 4,665,064 | A | 5/1987 | Hider et al. .......... 514/184 |
| 4,666,927 | A | 5/1987 | Hider et al. .......... 514/350 |
| 4,834,983 | A | 5/1989 | Hider et al. .......... 424/463 |
| 4,840,958 | A | 6/1989 | Hider et al. .......... 514/348 |
| 4,861,767 | A | 8/1989 | Hider et al. .......... 514/184 |
| 4,866,052 | A | 9/1989 | Hider et al. .......... 514/184 |
| 4,912,118 | A | 3/1990 | Hider et al. .......... 514/332 |
| 5,028,411 | A | 7/1991 | Callingham et al. .... 424/45 |
| 5,104,865 | A | 4/1992 | Hider et al. .......... 514/188 |
| 5,177,068 | A | 1/1993 | Callingham et al. .... 514/184 |
| RE34,313 | E | 7/1993 | Hider et al. .......... 514/188 |
| 5,256,676 | A | 10/1993 | Hider et al. .......... 514/348 |
| 5,480,894 | A | 1/1996 | Hider et al. .......... 514/348 |
| RE35,948 | E | 11/1998 | Hider et al. .......... 514/348 |
| RE36,831 | E | 8/2000 | Hider et al. .......... 514/188 |
| 6,197,763 | B1 | 3/2001 | Hepworth Thompson et al. .......... 514/184 |
| 6,339,080 | B1 | 1/2002 | Stockham et al. ...... 514/184 |
| 6,635,631 | B1 | 10/2003 | Stockham et al. ...... 514/184 |

FOREIGN PATENT DOCUMENTS

| EP | 0 159 194 | 10/1985 |
| EP | 0 159 917 | 10/1985 |
| EP | 0 247 980 B1 | 8/1991 |
| GB | 1178874 | 1/1970 |
| GB | 2 128 998 | 5/1984 |
| GB | 2 157 686 | 10/1985 |
| JP | 03 067 565 | 3/1991 |
| WO | WO 96/41627 | 12/1996 |
| WO | WO 98/16218 | 4/1998 |

OTHER PUBLICATIONS

Webster's New World Dictionary, Simon & Schuster, Inc., Third College edition, 1988, p. 1012, definition for "pharmaceutical."*
Ahmet, M.T., et al., "A Potential Iron Pharmaceutical Composition for the Treatment of Iron-deficiency Anaemia. The Crystal and Molecular Structure of mer-Tris-(3-hydroxy-2-methyl-4H-pyran-4-onato) iron (III)," J. Chem. Soc. Dalton Trans. 1159-1163, Royal Society of Chemistry (1988).
El-Jammal, A. and Templeton, D.M., "Reversed-phase high-performance liquid chromatography of non-transferrin-bound iron and some hydroxypyridone and hydroxypyrone chelators," J. Chromatography B. 658:121-127, Elsevier Science (Aug. 1994).
Luca, C., et al., "The Amphionic Structure of 3-Hydroxy-2-methyl-4H-pyran-4-one and the properties of its Complexes with Iron Ions," Revue Roumaine De Chimie, Bukarest, RO, vol. 38, No. 1, pp. 123-130 (1993).
Rice-Evans, C. and Baysal, E., "Iron-mediated oxidative stress in erythrocytes," Biochem. J. 244:191-196, Portland Press on Behalf of the Biochemical Society (1987).

(Continued)

Primary Examiner—John Pak
(74) Attorney, Agent, or Firm—Sterne, Kessler, Goldstein & Fox P.L.L.C.

(57) ABSTRACT

Compositions in solid form, such as powders, comprising a mixture of a ferrous salt and a hydroxypyrone maybe used to increase the level of iron in a patient's bloodstream or to treat and/or prevent gastrointestinal infection.

21 Claims, No Drawings

OTHER PUBLICATIONS

Seeberg, V.P., et al., "Hemoglobin Regeneration Following Oral Administration of Chelated Iron," *Science* 119:608-609, American Association for the Advancement of Science (1954).

Stefanović, A., et al., "On the Reaction of Iron (III) with Maltol," Collection *Czechoslov. Chem. Commun.* 33:4198-4214, Nakladatelstvi Ceskoslovenski Akademie Ved (1968).

English language abstract of Japanese Patent No. 03 067 565, Dialog File 351, Derwent WPI Accession No. 91-128755 (1991).

English language abstract of Hoiman, J.M. et al., "Spectrophotometric study of the iron-meconic complexes," Glas. Hem. Drus., Beograd 31:311-324, (1966), Abstract Service (1970).

International Search Report for International Application No. PCT/GB96/01382, issued Jan. 30, 1997.

International Search Report for International Application No. PCT/GB01/04052, issued Feb. 12, 2002.

Search report for GB 9922921.3, issued by the United Kingdom Patent Office Jan. 25, 2000.

English language abstract of European Patent No. 0 247 980 B1, Dialog File 351, Derwent WPI Accession No. 7072832 (1991).

Webster's New World Dictionary, Merriam-Webster, Inc., Tenth Edition, 2001, p. 1288, definition for "unit."

* cited by examiner

IRON COMPOSITIONS

CROSS-REFERENCE TO RELATED APPLICATIONS

This application is the § 371 U.S. National Phase Entry of International Application No. PCT/GB01/04052, filed Sep. 10, 2001 and published under PCT Article 21(2) in English, the entire contents of which are hereby incorporated by reference.

This invention relates to compositions which comprise iron ions to methods of making them and to their medical applications.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born. Moreover, in certain pathological conditions where there is blood loss, or where there is a mal-distribution of iron in the body, there may be a state of chronic anaemia. This is seen in diseases such as Crohn's disease, rheumatoid arthritis, certain haemolytic diseases and cancer.

Iron in the ferrous state ($Fe^{II}$) is a strong reducing agent and can also interact with, and damage, proteins, carbohydrates and lipids and can therefore be harmful to the body. It has been thought, therefore, that iron is best delivered to the body and kept in the body in the ferric state ($Fe^{III}$). However, it is difficult to do this because the solubility of ferric iron, and therefore its bioabsorption, is poor. The absorption rate of ferrous salts such as ferrous sulphate is typically 30% when given on an empty stomach but this causes unpleasant side effects particularly with chronic medication. When given with food, the absorption may fall to 1 to 3% of the administered dose. For some anaemias, a daily uptake of 30 milligrams of iron is required, and although a wide range of iron compounds is already marketed for the treatment of iron deficiency anaemia, the poor levels of iron uptake by the body from these compounds necessitates relatively high dosage levels. However, the administration of high doses of poorly absorbed iron complexes may cause siderosis of the gut wall and a variety of side effects such as stomach pains, nausea, vomiting, constipation and heavy black stools which can result in poor patient compliance with their treatment.

GB 2128998 and EP 0159194 describe neutral ferric iron complexes of various 3-hydroxy-4-pyrones in an iron:hydroxypyrone molar ratio of 1:3. The complexes are described for use at relatively low dosage levels for ferric compounds in the treatment of iron deficiency anaemia. In the body, these complexes were considered to be transferred into the gastrointestinal cell and then to dissociate to provide iron for absorption and transfer onto the body's natural uptake processes. However, the complexes of iron described in the above documents suffer from the significant problem that if dissociation of the complex occurs in an unfavourable environment in the body, particularly the gastrointestinal tract, native iron can be formed which precipitates and is therefore not absorbed.

GB 2128998 teaches that only a neutral complex comprising maltol and iron in the ferric state in a molar ratio of 3:1 (maltol:iron) confers a therapeutic effect. By contrast, charged complexes having maltol:iron molar ratios of 1:1 or 2:1 are shown by in vitro tests to be unsatisfactory so that iron from these complexes would not be expected to be taken up to a satisfactory extent in vivo, making them unsuitable for use in medicine.

WO 96/41627 describes ferric iron complexes of hydroxypyrones, which comprise a carboxylic acid such as citric acid. The compositions are useful for the treatment of iron deficiency anaemia.

The use of certain metal ion complexes for treating gastrointestinal infection with *Helicobacter pylori* is taught in WO98/16218. The complexes include complexes of iron in the ferric state.

U.S. Pat. No. 4,575,502 discloses pharmaceutical compositions containing an iron complex of a 3-hydroxy-4-pyrone. The iron is in the ferric state. Ferrous iron is taught away from on account of the instability of the ferrous complexes.

Iron-enriched foods which contain maltol or ethylmaltol are taught in JP-A-03-067565. The foods contain insufficient iron to provide an effective therapeutic treatment of anaemia or of other ailments.

Ferrous sulphate is widely used for the treatment of iron-deficiency anaemia. However, although it has a high solubility in the acidic environment found in the stomach and a good bioavailability, it suffers from the disadvantage that, at the near neutral pH in the duodenum, where iron is best absorbed, it is readily precipitated as ferric hydroxide. Furthermore, it can generate sulphuric acid and thus lead to toxicity. Ferrous succinate, gluconate and fumarate are standard therapeutic alternatives to ferrous sulphate but are all poorly and slowly soluble in water. All of these ferrous salts have undesirable side effects at the therapeutic dose (about 200 mg as iron per day) in a significant number of patients.

The present invention aims to alleviate some of the problems of existing iron-containing pharmaceutical compositions.

According to the invention in a first aspect, there is provided a composition which is in the form of a solid and which comprises a mixture of a ferrous salt and a hydroxypyrone.

Surprisingly, solid mixtures of ferrous salts and hydroxypyrones are stable on storage for a moderate period of time under substantially dry conditions. However, on dissolution in water, the compositions undergo a reaction in which some or all of the ferrous iron is oxidised to ferric iron. Thus, the compositions of the invention can exhibit the advantages that ferrous iron compositions possess prior to administration to a patient, including their ready availability in pharmaceutically acceptable form (eg, high purity), their relatively low cost and their lack of strong colour (allowing the colour of the compositions to be more readily modified for appeal to the customer and/or the patient), whilst retaining the advantages of ferric hydroxypyrone complexes in vivo as a result of their conversion to ferric complexes after administration to a patient. The advantages of the soluble ferric hydroxypyrone complexes include greater bioavailability and less damage to the mucosal wall of the gastrointestinal tract than the ferrous compositions and, therefore, reduced dosage.

The ferrous salt can be an iron (II) salt with any pharmaceutically acceptable anion. Preferably, the iron (II) salt is iron (II) carbonate or an iron (II) carboxylate. Suitable iron (II) carboxylates include, for example, iron (II) gluconate, iron (II) succinate and iron (II) fumarate. These ferrous salts are readily available at pharmaceutically acceptable levels of purity.

The hydroxypyrone is preferably a 3-hydroxy4-pyrone. Suitable pyrones include 3-hydroxy-4-pyrone itself or a 3-hydroxy-4-pyrone in which one or more of the hydrogen atoms attached to ring carbon atoms are replaced by an aliphatic hydrocarbon group of 1 to 6 carbon atoms, or a 5-hydroxypyrone, such as Kojic acid. The most preferred pyrones are maltol and ethylmaltol. The hydroxypyrone may, alternatively, be a natural product (such as meconic acid or iso-maltol) which may be converted to another hydroxypyrone in vivo.

Certain hydroxypyrones, such as maltol, are available commercially. With others, a convenient starting material in many instances consists of 3-hydroxy-4-pyrone which is readily obtainable by the decarboxylation of 2,6-dicarboxy-3-hydroxy-4-pyrone (meconic acid). For example, 3-hydroxy-4-pyrone may be reacted with an aldehyde to insert a 1-hydroxyalkyl group at the 2-position, which group may then be reduced to produce a 2-alkyl-3-hydroxy-4-pyrone. The preparation of 2-ethyl-3-hydroxy-4-pyrone, etc, by this route is described in the published U.S. application Ser. No. 310,141 (series of 1960). Other preparation methods are described by Spielman, Freifelder, J. Am. Chem. Soc. Vol 69 Page 2908 (1947).

It will be appreciated by skilled persons that these are not the only routes available to these compounds and their iron complexes and that various alternatives may be used.

The molar ratio of the ferrous salt to the hydroxypyrone in the compositions of the invention is preferably from 1:1 to 1:4. When the ratio of ferrous salt to hydroxypyrone is at the lower end of this range, for instance about 1:4, the composition does not necessarily require any further components to enhance the solubility of the iron. When the ratio of ferrous salt to hydroxypyrone is from 1:1 to 1: less than 4, on the other hand, the composition may further contain a carboxylic acid and/or a carboxylate ion (separate from, or in addition to, any carboxylate ion present in the ferrous salt) as is taught for ferric complexes in WO 96/41627, the disclosure of which is incorporated by reference herein.

The carboxylic acid or carboxylate ion may be present in the composition in a relatively small amount or in a large excess. Preferably, however, the molar ratio of carboxylic acid or carboxylate to ferrous salt is from 0.01:1 to 3:1. The carboxylate ion may be the same anion which is present, together with ferrous ions, in the ferrous salt, when the ferrous salt is a ferrous carboxylate.

Preferably, the carboxylic acid is, or the carboxylate ion is derived from, a $C_1$ to $C_6$ acid, particularly $C_1$ to $C_6$ having from 1 to $_3$ carboxylic acid groups.

Preferably the acid is selected from, or the carboxylate ion is derived from, one or more of citric acid, isocitric acid, gluconic acid, succinic acid, fumaric acid and tartaric acid. Of these acids, citric acid, gluconic acid, succinic acid and fumaric acid are particularly preferred. Conveniently, it is the tri-basic acid, citric acid, and is present in a formulation in an amount sufficient to generate a concentration in solution in the blood of from 0.1 to 100 mM following administration, preferably in an amount of 10 to 1000 mg per dose. The citric acid may be present as ammonium citrate or ferrous ammonium citrate.

As in the compositions of WO 96/41627, in solution the carboxylic acid may behave as a counter ion (anion) to the iron/hydroxypyrone complex, helping to maintain more iron in solution and available for absorption.

Conveniently, the composition of the invention is in the form of a powder (which term covers fine powders and granulates) comprising a mixture of the powdered hydroxypyrone. The ferrous salt and the hydroxypyrone may be in crystalline form, in amorphous form or in other solid forms but are preferably crystalline. The ferrous salt may contain water of crystallisation ie, it may be in the form of a hydrate.

In a further aspect, the compositions of the invention are used in medicine and, in another aspect, pharmaceutical compositions are provided which comprise the composition of the invention together with a pharmaceutically acceptable diluent or carrier.

The pharmaceutical composition of the invention may be adapted for oral administration. Suitable forms for oral administration include powders, tablets and capsules (such as gelatin capsules).

Suitable pharmaceutically acceptable diluents and carriers include, for example, lubricants such as magnesium stearate, stabilising and suspending agents such as methylcellulose and povidone and other tableting agents and dose bulking agents such as lactose and flow aids such as Aerosil 2000™. Particularly useful diluents and carriers are wetting agents or surfactants, preferably nonionic or ionic surfactants. Examples of suitable nonionic surfactants include polyoxyl 10 oleyl ether and polysorbates. An example of a suitable ionic surfactant is sodium lauryl sulphate.

Alternatively, the pharmaceutical composition may be provided as a suspension in liquid form, as a powder for reconstitution prior to oral or parental administration or it may be formulated for use as a suppository.

More than one iron complex of the invention may be contained in the pharmaceutical composition of the invention, and other active compounds may also be included. Typical additives include compounds having the ability to facilitate the treatment of anaemia such as folic acid. A source of zinc may also be included.

In a yet further aspect, the present invention provides the use of the composition of the invention in the manufacture of a medicament for increasing the level of iron in a patient's bloodstream or for the treatment and/or prevention of a gastrointestinal infection, such as with *Helicobacter pylori*.

Yet another aspect of the invention is a method of making a composition of the invention which comprises mixing a ferrous salt with a hydroxypyrone. The ferrous salt and the hydroxypyrone are preferably used in the method as powders and may be mixed using conventional mixers.

A still further aspect of the invention is a method of increasing the level of iron in a patient's bloodstream which comprises administering a composition of the invention to a patient. Also provided in another aspect is a method of treating and/or preventing a gastrointestinal infection (such as with *Helicobacter pylori*) which comprises administering a therapeutically effective amount of a composition of the invention to a patient in need thereof.

Surprisingly, the compositions of the invention have an increased rate of solution compared to the existing ferrous compositions which are suitable for oral administration. This increased rate of solution occurs over a wide pH range towards neutral. Rapid rate of solution is important since iron is most efficiently absorbed in the duodenum and, on an empty stomach, an ingested substance may reach the duodenum in less than 10 minutes. The compositions also improve on the existing ferrous compositions by allowing the overall dose of iron to be reduced to correct the iron deficiency anaemia and, in a manner similar to the ferric trimaltol complexes, they can be administered on an empty stomach so as to improve the bioavailability of the iron. Existing ferrous preparations cannot be administered on an empty stomach due to gastric intolerance in most patients and, in fact, have to be given with food which has the effect of reducing the uptake of iron. Absorption of from 1 to 6% of the dose of ferrous compositions is not uncommon, whereas absorption of the compositions of the invention may be as high as 20 to 30% of the dose administered.

Thus, the compositions of the invention can be administered at a reduced dose compared to the existing ferrous compositions. The reduced dose increases the safety margin of the products and reduces the likelihood of sensitivity to iron in patients.

The pharmaceutical compositions of the invention may be formulated in unit dosage form ie, in the form of discrete portions containing a unit dose, or a multiple or sub-unit dose. Preferably, the compositions of the invention are formulated to give a rapid release of the composition for optimal absorption in the body. Whilst the dosage of the composition given in each particular case will depend upon various factors, including the particular components of the composition, it may be stated by way of guidance that maintenance at a satisfactory level of the amount of iron present in the human (or animal) body will often be achieved using a daily dosage, in terms of the iron content of the compound, which lies in a range from about 1 to 150 mg, such as from 10 to 120 mg. However, it may be appropriate in certain cases to give daily dosages either below or above these levels. Compositions containing 20 to 50 mg iron, to be taken once daily, twice daily or three times daily (depending on the severity of the anaemia) are, for example, suitable for the treatment of anaemia. This represents a reduction in the conventional daily dose of ferrous iron of at least 50%.

The compositions of the invention suitably contain from 0.1% to 20% by weight iron, such as 0.1% to 10% by weight, for example, preferably 2 to 10% by weight.

The following non-limiting examples illustrate the invention.

EXAMPLES

Example 1

Compositions according to the invention were formulated by mixing ferrous gluconate (300 mg) with maltol (from 100 to 250 mg). The compositions contain about 35 mg iron.

At 100 mg maltol, there is likely to be mostly ferric maltol in solution. At 250 mg, there is likely to be mostly ferric trimaltol in solution.

Example 2

Example 1 was repeated using 170 mg ferrous gluconate and 60 to 150 mg maltol to give a composition containing about 20 mg iron. This lower dose composition is suitable for the prevention of anemia.

Example 3

Compositions were formulated by mixing ferrous gluconate (300 mg) with maltol (100 to 250 mg).

Example 4

Compositions were formulated by mixing ferrous fumarate (110 mg) with maltol (100 to 250 mg).

Example 5

Compositions were formulated by mixing ferrous carbonate (70 mg) with maltol (100 to 250 mg).

Example 6

The following is an example of a pharmaceutical composition according to the invention, which is suitable for formulation into gelatin capsules:

| Component | Amount (mg) |
|---|---|
| Ferrous gluconate | 240 |
| Maltol | 200 |
| Sodium lauryl sulphate | 2 |
| Lactose | balance to fill capsule |

Example 7

The following is also an example of a pharmaceutical composition according to the invention.

| Component | Amount (mg) |
|---|---|
| Ferrous gluconate | 240 |
| Maltol | 200 |
| Sodium lauryl sulphate | 2 |
| Magnesium stearate | 2 |
| Aerosil 2000 ™ | q.v. |
| Lactose | q.v. |

Example 8

Ferrous iron intolerant anaemic patients were treated with ferrous gluconate/maltol or ferrous fumarate/maltol compositions according to the invention. These patients were proven to be untreatable by standard oral ferrous iron preparations and their normal treatment would have been either by injection of an iron preparation or by blood transfusion. Both these treatments are normally used as a last resort due to potentially serious side effects. Furthermore, standard iron preparations would normally be contra-indicated in such patients due to the risk of exacerbating the underlying disease.

The planned duration of treatment was 3 months but patients were allowed to withdraw at any time of their own volition. 6 patients were allocated between the two treatments. 2 patients, one in each group, withdrew. One patient withdrew after 1 week with relatively mild gastrointestinal symptoms; the other patient withdrew because of a bleeding episode related to the underlying disease. One of the patients withdrawing was showing a good haematological response even after 1 week.

Four out of the six patients completed the treatment course and were considered to be asymptomatic for the side effects they normally associated with iron treatment. One patient failed to respond to treatment but from the clinical diagnosis prior to inclusion it was suspected the anaemia was of an unresponsive type to oral iron. Although this was confirmed the patient was allowed to continue and was assessed for tolerance to the new treatment.

Four out of the six patients showed an improvement in the anaemia with two classified as a full response as measured by the haemoglobin in excess of 13 g/dl and a rise in serum ferritin of 20 µg/L. One patient showed a 4 g/dl rise in haemoglobin levels. Two patients maintained their Hb levels over the period of treatment in excess of 11 g/dl when a fall would have been expected due to blood loss. Analysis of the data of the other two patients suggested they would probably have achieved a good response, as their iron stores were increasing, if a higher dose had been used or the treatment period had been extended.

The tests showed that both ferrous gluconate/maltol and ferrous fumarate/maltol pharmaceutical compositions produced a satisfactory tolerance profile and clinical response in 66% of patients previously classified as ferrous intolerant patients. An even higher number of positive results would be expected in less difficult iron intolerant anaemic patients. The data are particularly impressive when the treatment protocol of administering the medication on an empty stomach is taken into account.

The invention claimed is:

1. A pharmaceutical composition which is in the form of a solid that is in the form of a powder and which comprises a mixture of a ferrous salt and a hydroxypyrone, in an amount effective to increase the level of iron in a patient's bloodstream, together with a pharmaceutically acceptable diluent or carrier.

2. A pharmaceutical composition as claimed in claim 1, wherein said ferrous salt is an iron (II) carboxylate.

3. A pharmaceutical composition as claimed in claim 2, wherein said ferrous salt is selected from the group consisting of iron (II) gluconate, iron (II) succinate and iron (II) fumarate.

4. A pharmaceutical composition as claimed in claim 1, wherein said ferrous salt is iron (II) carbonate.

5. A pharmaceutical composition as claimed in any one of claims 1 to 4, wherein said hydroxypyrone is a 3-hydroxy-4-pyrone.

6. A pharmaceutical composition as claimed in claim 5, wherein said hydroxypyrone is maltol or ethylmaltol.

7. A pharmaceutical composition as claimed in claim 1, wherein the molar ratio of ferrous salt to hydroxypyrone is from 1:1 to 1:4.

8. A pharmaceutical composition as claimed in claim 7, wherein said molar ratio of ferrous salt to hydroxypyrone is about 1:3.

9. A pharmaceutical composition as claimed in claim 7, wherein said molar ratio of ferrous salt to hydroxypyrone is from 1:1 to 1: less than 3 and the composition further comprises a carboxylic acid.

10. A pharmaceutical composition as claimed in claim 9, wherein said carboxylic acid is citric acid or tartaric acid.

11. A pharmaceutical composition as claimed in claim 10, wherein the molar ratio of carboxylic acid to ferrous salt is from 0.01:1 to 3:1.

12. A pharmaceutical composition as claimed in claim 1 which further comprises a wetting agent or surfactant.

13. A pharmaceutical composition as claimed in claim 1 for use in medicine.

14. A pharmaceutical composition as claimed in claim 1, wherein the powder is formulated into a tablet or capsule for oral administration.

15. A method of use of a pharmaceutical composition as claimed in claim 1 in the manufacture of a medicament for increasing the level of iron in a patient's bloodstream which comprises mixing said mixture of ferrous salt and hydroxypyrone in an amount effective to increase the level of iron in a patient's bloodstream with a said pharmaceutically acceptable diluent or carrier.

16. A method of making a pharmaceutical composition of claim 1 which is in the form of a solid that is in the form of a powder, which comprises mixing said ferrous salt with said hydroxypyrone in an amount effective to increase the level of iron in a patient's bloodstream, together with a pharmaceutically acceptable diluent or carrier.

17. A method of increasing the level of iron in a patient's bloodstream which comprises administering a composition of claim 1 to the patient.

18. A pharmaceutical composition as claimed in claim 1, further comprising one or more compounds for the treatment of anaemia.

19. A pharmaceutical composition as claimed in claim 18, wherein said one or more compounds comprises folic acid.

20. A pharmaceutical composition as claimed in claim 1, further comprising zinc.

21. A method of increasing the level of iron in a patient's bloodstream which comprises administering to said patient a pharmaceutical composition which is in the form of a solid and which comprises a mixture of a ferrous salt and a hydroxypyrone in an amount effective to increase the level of iron in the patient's bloodstream, together with a pharmaceutically acceptable diluent or carrier, wherein said composition is administered orally on an empty stomach without food.

* * * * *